United States Patent [19]

Abken et al.

[11] Patent Number: 5,674,723
[45] Date of Patent: Oct. 7, 1997

[54] NUCLEIC ACID MOLECULES WHICH IMMORTALIZE HUMAN OR ANIMAL CELLS AND USES THEREOF

[75] Inventors: Hinrich Johann Abken, Bonn; Klaus Willecke, Essen; Herbert Jungfer, Starnberg; Heinrich Barchet, Bernried, all of Germany

[73] Assignee: Boehringer Mannheim GmbH, Mannheim, Germany

[21] Appl. No.: 382,933

[22] Filed: Feb. 2, 1995

Related U.S. Application Data

[63] Continuation of Ser. No. 72,745, Jun. 7, 1993, abandoned.

[30] Foreign Application Priority Data

Jun. 10, 1992 [DE] Germany .................... 42 18 945.4

[51] Int. Cl.⁶ .................... C12N 15/64; C12N 5/16; C12N 15/11; C12P 19/34
[52] U.S. Cl. .................... 435/172.3; 435/91.2; 435/91.32; 435/325; 435/372; 435/320.1; 536/23.1; 536/24.33
[58] Field of Search .................... 435/91.2, 91.32, 435/172.1, 172.3, 240.2, 325, 372, 320.1; 536/23.1, 24.31, 24.33

[56] References Cited

U.S. PATENT DOCUMENTS

4,472,502  9/1984  Snow et al. .................... 435/172.3

OTHER PUBLICATIONS

Abken et al. (1988), PNAS USA, 85, 468–472.
Abken et al. (1990), in "Growth Regulation and Carcinogenesis", vol. 1 ed. Paukovits, CRC Press pp. 234–241.
Sambrook et al. (1989) "Molecular Cloning: A Laboratory Manual, 2nd Edition", pp. 1.42, 1.43, 9.27, 13.3, 13.6 CSH Press.

Primary Examiner—Mindy Fleisher
Assistant Examiner—Terry A. McKelvey
Attorney, Agent, or Firm—Felfe & Lynch

[57] ABSTRACT

The present invention concerns DNA sequences which are suitable for immortalizing human or animal cells, processes for isolating such DNA sequences as well as processes for producing immortalized human or animal cells using such a DNA.

17 Claims, No Drawings

NUCLEIC ACID MOLECULES WHICH IMMORTALIZE HUMAN OR ANIMAL CELLS AND USES THEREOF

This application is a continuation of application Ser. No. 08/072,745, filed Jun. 7, 1993, now abandoned.

FIELD OF THE INVENTION

The invention concerns nucleic acid molecules; such as DNA sequences which are suitable for the immortalization of human or animal cells, processes for the isolation of such DNA sequences as well as processes for producing immortalized human or animal cells using such a DNA.

BACKGROUND AND PRIOR ART

Normal human and animal cells only have limited viability and ability to divide in culture. The onset of cell aging in the culture depends on the degree of differentiation of the cell, the age and species of the donor as well as on the duration of the culture. Aging cells stop dividing and cease to synthesise special cell products such as e.g. antibodies, hormones or growth factors. The cell products obtained from such normal human and animal cells always have significant advantages compared to products produced by recombinant means when for example differentiation-specific and/or species-specific secondary modifications, such as glycosylation, are important for their biological effectiveness. So-called cell lines proliferate indefinitely in culture. This enables these cell lines to be cultured in any number and the isolation of cell products in unlimited amounts. However, since most cell lines have been established from malignant tumours these cells, which are capable of dividing permanently, express a multitude of tumour cell properties but have also lost some of the properties of normal cells which can only be cultured to a limited extent. These include the ability to produce special cell products such as those listed above. Therefore in order to isolate cell products from highly differentiated cells, methods have been developed with which normal, non-tumorigenic cells can be kept in culture as cell lines over a long period by immortalization.

Long-term cultures of human B-lymphocytes as well as T-lymphocytes can be maintained by repeated stimulation by substances which stimulate cell division (mitogens). The mitogens used for this include polyclonal B-cell activators, combination of phorbol esters and a potassium ionophore or specific growth factors (cytokines) in combination with immobilized anti-B cell antibodies (J. Immunol. 141 (1988), 164; Science 251 (1991), 70 and J. Exp. Med. 170 (1989), 877)). However, in these methods the growth of the cells remains dependent on the addition of cytokines or on repeated mitogenic stimulation.

Another method for immortalizing human or animal cells is to infect such cells with transforming viruses. However, in this process the cells lose some of the properties of normal cells, and, in addition express properties of tumour cells capable of permanent division. Thus, for example, lymphocytes remain in an early differentiation stage of B-cell development after infection with the Epstein-Bart virus (EBV). Thus after EBV infection of human B-lymphocytes in vitro cell clones are often obtained which produce IgM in very low amounts or even no immunoglobulins at all. When cultured further in vitro the EBV-infected B-cells which at first produced immunoglobulins often lose the ability to synthesize immunoglobulin. For this reason, EBV-infected B-lymphocytes are hardly suitable for the isolation of specific antibodies in larger amounts when a constant rate of synthesis by the cells over a long culture period is desired.

The same applies to the immortalization of mouse B lymphocytes by infection with the Abelson leukemia virus.

A further technique for the immortalization of cells is cell—cell fusion (Köhler and Milstein, Nature 256 (1975), 495). In this process normal lymphocytes with a limited ability to divide are fused with permanently growing cell lines (myeloma cell lines, lymphoma cell lines, lymphoblastic cell lines infected with Epstein-Barr virus). The use of suitable selection media ensures that the hybrid cells obtained can proliferate preferentially, but that the fusion partners themselves die off. The hybrid cells obtained can be cloned by preparing single-cell cultures and the cell clones which secrete the desired product can be proliferated for large-scale production. Since the hybrid cells have a double set of chromosomes of the initial cell they tend to lose chromosomes (usually those of the normal starting cell) in the following cell generations. In this process the desired properties of the hybrid cells (in particular the production of the desired cell product) can again be lost. Thus the disadvantages of the hybridoma technique are the time-consuming selection of the desired hybrid cells, synthesis of hybrid cell products if they are multi-chained proteins and loss of chromosomes which can lead to loss of the synthesis of the desired cell product.

An improvement of this method is described in EP-B 0 093 436. According to this reference, cells are immortalized by fusion with a fragment of a transformed cell which is itself not capable of proliferation. The resulting fusion product is capable of dividing indefinitely in culture. In this case fractions of the cytoplasm, preferably cytoplasts, serve as the fragment which is no longer capable of proliferation. Since the cytoplasmic fragments used do not proliferate in culture, selection of the hybrid cell is superfluous.

Moreover the above-mentioned disadvantages of the cell cell hybrids such as loss of chromosomes and consequently loss of the desired cell properties and of synthesis of hybrid cell products does not occur in the cell lines obtained in this way. A further development of this method is described in EP-A 0 256 512. This application teaches that a DNA fraction is first isolated from the cytoplasm, preferably from the cytoplasts, of cells which are capable of dividing permanently. The cells to be immortalized are then transfected with this DNA. By this means an increase in the yield of immortalized cells is achieved. This method also leads to the establishment of immortalized cell lines while avoiding the disadvantages of the hybridoma technique. However, the isolation of the immortalizing DNA from a mitochondria-free cytoplasmic fraction is time-consuming and necessitates several purification steps. Moreover the yield of the DNA obtained in this way is low. Thus, for example, with the aid of suitable isolation methods a maximum of 200 ng DNA can be isolated from the cytoplasm of $10^9$ L929 cells. This amount of DNA is only sufficient to establish about 30 cell clones after transfection of $10^8$ lymphocytes.

SUMMARY OF THE INVENTION

Therefore the object of the present invention was to provide nucleic acid molecules such as DNA in large amounts and in a pure form for the immortalization of human or animal cells. This object is achieved by a DNA which is suitable for immortalizing human or animal cells and is obtainable by isolating a mitochondria-free cytoplasmic fraction from permanently culturable human or animal cells, treating this cytoplasmic fraction with RNase and proteinase, isolating a DNA fraction which has a density of about 1.86 g/cm³ in a CsCl gradient therefrom and isolating a DNA from this DNA fraction which hybridizes with the DNA sequence shown in SEQ ID NO:1 and/or SEQ ID NO:2.

A preferred embodiment of the present invention is a DNA which has the sequence set forth in SEQ ID NO:1 as well as a DNA which has the sequence set forth in SEQ ID NO:2.

Surprisingly it turned out that efficient immortalization of human or animal cells is possible using these DNA sequences. This DNA is available in any required amount for immortalizing human or animal cells by cloning the immortalizing DNA according to the present invention.

These DNA sequences can be obtained from the cytoplasm of permanently culturable human or animal cells. Cytoplasts of tumour cells are preferably used for this. Cytoplasts of transformed mouse L cells (L929 cells, ATCC CCL 1) or Ehrlich ascites cells (EAC, ATCC CCL 77) are particularly preferred. However, other tumour cell lines familiar to a person skilled in the art and immortalized non-tumorigenic cell lines can also be used. The cytoplasts are obtained and lysed according to known methods (Wigler and Weinstein, Blochem. Biophys. Res. Comm. 63 (1975), 669–674). Lysis is carried out for example by repeated freezing and thawing or by lysis of the cells in the presence of 50 mmol/l Tris-HCl pH 7.5, 10 mmol/l EDTA, 1.5 mmol/l MgCl$_2$. The mitochondria are separated from the cytoplast fraction preferably with the aid of a sucrose gradient (J. Biol. Chem. 249 (1974), 7991–7995). The fractions which do not contain mitochondria are incubated with RNase, preferably RNaseA and RNaseT1, and subsequently with proteinase, preferably proteinase K. The DNA is isolated according to known methods from this preparation and a fraction which has a density of about 1.86 g/cm$^3$ in a cesium chloride gradient is concentrated. This concentration is preferably carried out using a CsCl density gradient or by means of electrophoretic separation according to a method familiar to a person skilled in the art (Sambrook et al. Molecular Cloning, Cold Spring Harbor Laboratory, Second Edition 1989). The DNA fraction obtained in this way is cloned in vectors familiar to a person skilled in the art such as for example pUC19 and amplified in host organisms which are likewise familiar to an expert such as for example E. coli HB101 or DH5α. The recombinant plasmids which contain a DNA sequence according to the present invention are identified by hybridization with the DNA sequence shown in SEQ ID NO:1 or that in SEQ ID NO:2, where the hybridization is carried out under stringent conditions, as elaborated upon infra. In doing so it surprisingly turned out that only one of 28 independent recombinant plasmid clones of the DNA fraction with a density of about 1.86 g/cm$^3$ from L929 cells (pLC108) and one of 25 recombinant plasmid clones of the respective DNA fraction from Ehrlich ascites cells (pEFC38) contain a DNA which is suitable for immortalizing human or animal cells. The sequence of this DNA is shown in SEQ ID NO:1 (insert of pLC108) and SEQ ID NO:2 (insert of pEFC38). With the aid of these sequences it is then easily possible to find further DNA sequences suitable for immortalizing human or animal cells.

Thus the present invention in addition concerns a process for the isolation of a DNA which is suitable for immortalizing human or animal cells wherein this process is characterized in that a mitochondria-free cytoplasmic fraction is isolated from permanently culturable human or animal cells, this cytoplasmic fraction is treated with RNase and proteinase, a fraction which has a density of about 1.86 g/cm$^3$ in a CsCl gradient is isolated therefrom and a DNA is isolated from this DNA fraction which hybridizes with the DNA sequence shown in SEQ ID NO:1 and/or SEQ ID NO:2. Hybridization is carried out with the recited sequence under stringent conditions. The term "stringent conditions" refers to the parameters recited in Maniatis et al., Molecular Cloning, A Laboratory Manual (Cold Spring Harbor Laboratory, 1982), pages 387–389, the disclosure of which is incorporated by reference in its entirety. In particular, however, suitable stringent conditions include the use of a hybridization solution (6×SSC, 0.01M EDTA, $^{32}$P labelled probe DNA, 5×Denhardt's solution, 0.5% SDS, and 100 µg/ml denatured salmon sperm DNA). Hybridization can be carried out in a water bath at 68° C. Final washes (2) can take place in 0.1×SSC, 0.5% SDS, at 68° C. This teaching sets forth particular conditions of stringency, it being understood that the same degree of stringency may be achieved even with variations of the parameters.

The cytoplasmic fraction used for isolating this DNA can be obtained as described above by repeated freezing and thawing or by lysing the cells in the presence of 50 mmol/l Tris-HCl pH 7.5, 10 mmol/l EDTA, 1.5 mmol/1 MgCl$_2$. Alternatively a cell fraction which is free of nuclear DNA can also be used. Such a fraction is preferably obtained by lysing the cells with NaCl and SDS (Hirt Extraction, J. Mol. Biol. 26 (1967), 365–369) and subsequent centrifugation. The immortalizing DNA sequences can then be obtained from the supernatant.

The DNA sequences according to the present invention can in addition also be obtained from a genomic gene library or a cDNA library of human or animal cells. In this case the DNA sequences shown in SEQ ID NO:1 and/or SEQ ID NO:2 are used as a hybridization probe to identify a DNA sequence according to the present invention in the gene library. Gene libraries of permanently growing cells and also those of normal non-immortalizing cells can be used for this.

Thus the present invention in addition concerns a process for the isolation of a DNA which is suitable for immortalizing animal or human cells wherein this method is characterized in that a genomic gene library or a cDNA library of human or animal cells hybridizes with the DNA sequence shown in SEQ ID NO:1 or SEQ ID NO:2 and the DNA hybridizing with one of these DNA sequences is isolated.

The present invention also concerns a process for isolating the DNA sequences according to the present invention which is characterized in that a DNA or RNA fraction of human or animal cells is amplified enzymatically whereby oligonucleotide starter molecules are used which are homologous to the sequence shown in SEQ ID NO:1 and/or SEQ ID NO:2. Oligonucleotide starter molecules are preferably used which have a length of 20 to 30 base pairs. The enzymatic amplification of the immortalizing DNA sequences using the polymerase chain reaction ("DNA polymerase chain reaction", PCR) is carried out according to methods known to a person skilled in the art (Mullis and Fallona, Meth. Enzymol. 155 (1987), 335–350; Saiki et al., Science 239 (1988), 487–491).

Gene libraries of permanently growing cells as well as those of normal non-immortalizing cells can be used as the DNA fraction for this. Furthermore a DNA or RNA preparation from any human or animal cells can be used in this method. The sequences of particularly preferred oligonucleotide starter molecules for amplifying the DNA sequence shown in SEQ ID NO:1 are shown in SEQ ID NO:3 and SEQ ID NO:4. The sequences of particularly preferred oligonucleotide starter molecules for amplifying the DNA sequence shown in SEQ ID NO:2 are set forth in SEQ ID NO: 5 and SEQ ID NO:6.

Finally the DNA sequences according to the present invention can also be chemically synthesized by commercial instruments for oligonucleotide synthesis.

Thus the present invention in addition concerns a process for the isolation of a DNA which is suitable for immortalizing human or animal cells wherein this process is characterized in that the DNA sequence shown in SEQ ID NO:1 or SEQ ID NO:2 is chemically synthesized.

In addition the present invention concerns a process for producing immortalized human or animal cells by transfection of normal human or animal cells with a DNA sequence according to the present invention or with a part of this sequence and culturing the transfected cells in a culture medium without selection substances. In this connection it surprisingly turned out that only 10–30 ng of a DNA according to the present invention are sufficient to obtain 30–40 immortalized lymphoid colonies when transfecting $10^8$ lymphocytes. Surprisingly the immortalizing effect could be further improved by a factor of 3–6 when the DNA sequences according to the present invention had been incubated with a protein fraction of permanently culturable cells before transfection.

Thus the present invention also concerns a process for the production of immortalized human or animal cells by transfecting normal human or animal cells with a DNA sequence according to the present invention or with part of this sequence which has been previously incubated with a protein fraction of permanently culturable human or animal cells wherein a 25000×g supernatant of the nuclear fraction or a 100000×g supernatant of the cytoplasmic fraction which has been pretreated with RNase is used as the protein fraction.

The protein fraction used for this is obtained from the nucleus or cytoplasm of the permanently culturable cells. For this the cells are firstly lysed by repeated freezing and thawing. Separation into nuclear and cytoplasmic fractions is carried out by centrifuging for 30 minutes at 6000×g. The sedimented cell nuclei are taken up in buffer and homogenized by sonification. After centrifuging for 30 minutes at 25000×g and 4° C., dialysis of the supernatant against PBS and subsequent digestion with RNase, the 25000×g supernatant of the nuclear fraction used in the process according to the present invention is obtained. The cytoplasmic fraction is centrifuged for one hour at 100000×g and 4° C., the supernatant is likewise dialyzed against PBS and digested with RNase.

Preincubation of the DNA according to the present invention with the 25000×g supernatant of the nuclear fraction or the 100000×g supernatant of the cytoplasmic fraction is carried out for 30 minutes at 4° C. in 10 mmol/l Tris-HCl pH 7.0, 10 mmol/l β-mercaptoethanol, 10 ng/ml tRNA, 66 ng/ml herring sperm DNA (1 mM ATP, 1 mM GTP) and either 80 mmol/l NaCl (if a DNA is used which hybridizes with the DNA sequence shown in SEQ ID NO 2) or 8 mmol/l $ZnCl_2$ (if a DNA is used which hybridizes with the DNA sequence shown in SEQ ID NO 1). Subsequently those proteins which did not bind to the respective DNA sequence are degraded by a one hour incubation with proteinase K (20 µg/ml) at 60° C.

The binding of the retained protein fraction to the DNA sequences according to the present invention is stable against high salt concentrations such as 6.9 mol/l CsCl and against further digestion by proteinase K (100 µg/ml, 1 hour at 60° C.). Thus the DNA protein particles obtained are more stable than the nucleosomes known from the chromosomes of the nucleus. An amplification of the DNA bound in these particles is nevertheless possible using taq polymerase.

The DNA sequences according to the present invention can be cloned and amplified by a person skilled in the art using common cloning systems. Even after cloning they are still able to immortalize human or animal cells.

Thus the present invention also concerns a process for the production of immortalized human or animal cells by transfecting normal human or animal cells with a cloned DNA sequence according to the present invention or part of this sequence. In this case those DNA sequences according to the present invention can be used in which individual bases of the said DNA sequences are replaced by others or by modified bases. In this way a higher stability of the DNA sequences according to the present invention can for example be achieved.

It surprisingly turned out that the DNA of a cell immortalized according to one of the aforementioned processes is also suitable for immortalizing human or animal cells.

Thus the present invention also concerns a process for the production of immortalized human or animal cells by transfecting normal human or animal cells with the total DNA from an immortalized cell obtainable according to one of the processes according to the present invention.

Furthermore, it surprisingly turned out that a better yield of immortalized lymphoid colonies is obtained when the cell to be immortalized is in a state stimulated for growth.

Thus the present invention in addition concerns a particular embodiment of the process according to the present invention for the production of immortalized human or animal cells wherein the cell to be immortalized is converted into a state stimulated for cell division before transfection with the DNA according to the present invention. The conversion of resting cells into such a state stimulated for growth (proliferation phase I, J. Cell Biol. 103 (1986), 795–805) is carried out according to methods known to a person skilled in the art, for example by addition of "pokeweed mitogen" or other mitogens or antigens to the culture medium.

The human lymphocytes immortalized with the DNA according to the present invention or by the process according to the present invention do not express a neoplastic transformed phenotype. Thus these cells do not form colonies in semi-solid agar medium. In contrast tumour cells grow in such a medium.

Growth in semi-solid agar medium can be induced by incubating the immortalized cells with carcinogenic substances in vitro or by irradiation with particle radiation or electromagnetic radiation. Thus the formation of colonies of immortalized cells in this medium is an indication of a possible transforming activity of the respective substance or particle radiation or electromagnetic radiation used.

Finally a further subject matter of the invention is the use of an immortalized cell obtained according to the process according to the present invention for the isolation of homologous or heterologous cell products, for testing active substances or particle radiation or electromagnetic radiation.

The present invention is elucidated further by the following examples in conjuction with the sequence protocols.

SEQ ID NO:1: shows a DNA sequence from L929 cells suitable for immortalizing human or animal cells.

SEQ ID NO:2: shows a DNA sequence from Ehrlich ascites cells suitable for immortalizing human or animal cells.

SEQ ID NO:3: shows a primer suitable for amplification of a DNA having the sequence shown in SEQ ID NO:1.

SEQ ID NO:4: shows a primer suitable for amplification of the DNA having the sequence shown in SEQ ID NO:1.

SEQ ID NO:5: shows a primer suitable for amplification of a DNA having the sequence shown in SEQ ID NO:2.

SEQ ID NO:6: shows a primer suitable for amplification of a DNA having the sequence shown in SEQ ID NO:2.

EXAMPLE 1

Isolation of a DNA which is Suitable for Immortalizing Normal Human or Animal Cells.

For the isolation of a DNA which is suitable for immortalizing normal human or animal cells, cytoplasts of transformed mouse L cells (L929 cells, ATCC CCL 1) or of Ehrlich ascites cells (EAC, ATCC CCL 77) are firstly isolated and lysed according to well-known methods (Wigler and Weinstein, Blochem. Biophys. Res. Comm. 63 (1975), 669–674). Lysis is carried out by repeated freezing and thawing. The mitochondria are separated from the cytoplast fraction with the aid of a sucrose gradient (J. Biol. Chem. 249 (1974), 7991–7995). The fractions which do not contain any mitochondria are incubated with RNaseA (20 μg/ml) and RNaseT1 (1000 U/ml) and subsequently with proteinase K (50 μg/ml). The DNA is isolated from this preparation according to known methods and a fraction which has a density of 1.86 g/cm$^3$ in a cesium chloride gradient is concentrated via a CsCl density gradient (Sambrook et al. Molecular Cloning, Cold Spring Harbor Laboratory, Second Edition 1989). The DNA fraction obtained in this way is cloned in pUC19 and amplified in *E. coli* HB101.

One of 28 independent recombinant plasmid clones of the DNA fraction with a density of 1.86 g/cm$^3$ obtained from L929 cells (pLC108) and one of 25 recombinant plasmid clones of the corresponding DNA fraction obtained from Ehrlich ascites cells (pEFC38) contains a DNA which is suitable for immortalizing human or animal cells. The sequence of this DNA is shown in SEQ ID NO:1 (insert of pLC108) and in SEQ ID NO:2 (insert of pEFC38).

EXAMPLE 2

Immortalization of human lymphocytes from peripheral blood by transfection with LC108 DNA (SEQ ID NO:1) or EFC38 DNA (SEQ ID NO:2)

1. Isolation of human lymphocytes from peripheral blood.

Peripheral blood of adult donors is diluted with a three-fold volume of a buffer consisting of 3 mmol/l citric acid, 100 mmol/l dextrose, 70 mmol/l NaCl and 30 mmol/l sodium citrate, pH 6.1. The lymphocytes are separated from the erythrocytes and from other nucleated cells by centrifugation in a Lymphoprep$^R$ gradient (Metrizoat, Nyegaard, Oslo) at 400 g for 35 min (A. Boyum, Scand. J. Clin. Invest. 21, Suppl. 97 (1968), 51–76). The lymphocytes obtained are washed twice in phosphate buffered saline (PBS, 136 mmol/l NaCl, 2.7 mmol/l KCl, 1.5 mmol/l KH$_2$PO$_4$, 6.5 mmol/l Na$_2$HPO$_4$, 0.4 mmol/l MgSO$_4$, 0.7 mmol/l CaCl$_2$, pH 7.4) and cultured in Iscove's DMEM with 4 mmol/l glutamine, 1 mmol/l pyruvate, 1 mmol/l oxaloacetic acid, 0.1 U/ml insulin, 10 μg/ml transferrin and 10% fetal calf serum at a cell density of 3×10$^6$ cells/ml at 37° C., 5% CO$_2$.

2. Transfer of the Immortalizing DNA Sequences into Human Lymphocytes.

The lymphocytes (3×10$^8$ cells) prepared according to example 2.1 are stimulated to cell division by "pokeweed mitogen" (PWM, 5 μg/ml) and one day later are divided into three parallel cultures (A, B, C), each of 10$^8$ cells. The cells of culture A are incubated with pLC108 DNA, the cells of culture B with pEFC38 DNA. The plasmids pLC108 and pEFC38 used in these cases contain the DNA sequence shown in SEQ ID NO:1 or SEQ ID NO:2 cloned into the BamHI site of pUC19. The cells of culture C are treated in the same way as cultures A and B except that no DNA to be transferred is present in the incubation medium.

70 μl HBS (20 mmol/l Hepes, 150 mmol/l NaCl, pH 7.4) is added to 30 μl transfection reagent DOTAP (1 mg/ml, Boehringer Mannheim GmbH, Cat. No. 1202 375) on a polystyrene petri dish. The DNA (200 ng) is dissolved in 100 μl HBS, added to the diluted transfection reagent and incubated for 10 min at room temperature. The lymphocytes to be transfected (10$^8$ cells in 3 ml Iscove's DMEM) are added. This preparation is incubated overnight at 37° C., 5% CO$_2$. The cells are washed once with PBS, sown at a density of 10$^7$ cells/ml in Iscove's DMEM with 4 mmol/l glutamine, 1 mmol/l pyruvate, 1 mmol/l oxaloacetic acid, 0.1 U/ml insulin, 10 μg/ml transferrin and 10% fetal calf serum in 96-well microtitre plates (100 μl/well) and cultured at 37° C., 5% CO$_2$ 0.50 μl culture medium is replaced by fresh medium during the next two weeks. In the fourth week 100 μl fresh medium is added. In the fifth week permanently growing colonies are visible which are transferred to 24-well petri dishes in the sixth week. The immortalized cell lines which are now maturing can be routinely subcultured in Iscove's DMEM every 7 days.

5 days after DNA transfer, lymphocyte colonies are observed in cultures A and B which increase in size and cell number (up to 1000 cells/colony) during the following days. These colonies disintegrate into several smaller colonies some of which start to grow continuously from about the third or fourth week after DNA transfer. In the fifth week after DNA transfer, colonies of lymphoid cells are recognizable in all the wells of the microtitre plate (Table 1). The cells are proliferated in culture for up to 6 months without any observable ageing of the cells.

In culture C (without DNA transfer) no proliferation of lymphocytes takes place and no continuously growing colonies of lymphoid cells are obtained. The cells therefore age within the first week and die.

TABLE 1

Immortalization of human lymphocytes by transfection with cloned pLC108 and pEFC38 DNA

| Culture | Lymphocytes used | Transfected DNA | (ng) | Immortal. lymphoid colonies | Immort. efficiency* colonies/ng DNA |
|---|---|---|---|---|---|
| A | 10$^8$ | pLC108 | 200 ng | 40 | 0.2 |
| B | 10$^8$ | pEFC38 | 200 ng | 50 | 0.25 |
| C | 10$^8$ | — | — | 0 | 0 |

*In determining the immortalizing efficiency the differing molar amounts of immortalizing DNA were not taken into account.

EXAMPLE 3

Immortalization of human lymphocytes by transferring enzymatically amplified LC108 and EFC38 DNA sequences.

The human lymphocytes were isolated from peripheral blood as described in example 2.1.

The immortalizing DNA sequences LC108 and EFC38 are amplified in a known manner (Mullis and Fallona, Meth. Enzymol. 155 (1987), 335–350; Saiki et al., Science 239 (1988), 487–491) using the polymerase chain reaction ("DNA polymerase chain reaction", PCR).

The plasmid DNA pLC108 and pEFC38 is linearized with the aid of the restriction endonuclease HindIII, precipitated with sodium acetate and ethanol and taken up in TE (10 mmol/l Tris, pH 7.5, 1 mmol/l EDTA).

The PCR reaction mixture (100 µl) contains:

10 µl 10× Taq buffer (200 mmol/l Tris-HCl, pH 8.4, 250 mmol/l KCl, 0.5% Tween 20, 1 mg/ml BSA), 1.5 µl 100 mmol/l MgCl$_2$, 2.5 µl dNTP solution (2 mmol/l dATP, 2 mmol/l dCTP, 2 mmol/l dGTP, 2 mmol/l dTTP), 2 U Taq polymerase (Boehringer Mannheim), 10 ng pLC108 or pEFC38 DNA as well as 100 ng of each of the primer oligonucleotides A and B for the amplification of LC108 DNA and primer oligonucleotides C and D for the amplification of EFC38 DNA.

The primer oligonucleotide sequences (primers) are homologous to the sequence LC108 (SEQ ID NO:1) or EFC38 (SEQ ID NO:2) according to the present invention.

Primer A: 5'GATCTTGAGTTTCCTCGTTGTAGGT 3' (SEQ ID NO:3)

Primer B: 5'GATCCAAAGCCCTCTGCTGGCCTCC 3' (SEQ ID NO:4)

Primer C: 5'GATCCAATCAGCTCAGCCACCCCCA 3' (SEQ ID NO:5)

Primer D: 5'GATCAAAACCAGGGCCTCCCACATG 3' (SEQ ID NO:6)

30 cycles with the following temperature profile are carried out:

1. 1×[5 min 95° C.]

2. 30×[30 sec 55° C.; 90 sec 72° C.; 60 sec 95° C.]

3. 1×[15 min 72° C.]

The DNA sequences LC108 (203 bp) and EFC38 (376 bp) amplified in this way are extracted with chloroform/isoamyl alcohol (24:1, v/v), precipitated with sodium acetate and ethanol, resuspended in TE pH 7.5 and used for the immortalization of human lymphocytes.

For this lymphocytes prepared according to example 2.1 (3×10$^8$ cells) are stimulated to cell division by pokeweed mitogen (5 µg/ml) and one day later are divided into three parallel cultures (A, B, C), each of 10$^8$ cells.

The cells of culture A are transfected with 10 ng of the PCR-amplified DNA sequence LC108, the cells of culture B with 10 ng of EFC38 DNA. DNA transfer and culture of the transfected cells is carried out as described in example 2.2. The cells of culture C are treated in the same way as the cells of cultures A and B except that no DNA to be transferred is present in the incubation medium.

3 to 4 weeks after transfection colonies of lymphoid cells are observed in cultures A and B which continuously increase in size. These colonies disintegrate in the fifth week and several smaller colonies of lymphoid cells grow which can be transferred into larger culture vessels in the sixth week (Table 2). The cells are routinely proliferated for several months in culture without an observable ageing of the cells. No continously growing colonies of lymphoid cells are obtained in culture C. The cells die within 5 days after pseudo DNA transfer.

TABLE 2

Immortalization of human lymphocytes by transferring enzymatically amplified LC108 or EFC38 DNA

| Culture | Lymphocytes used | Transfected DNA | (ng) | Immortal. lymphoid colonies | Immort. efficiency* colonies/ng DNA |
|---|---|---|---|---|---|
| A | 10$^8$ | LC108 | 10 ng | 35 | 3.5 |
| B | 10$^8$ | EFC38 | 24 ng | 34 | 1.4 |
| C | 10$^8$ | — | — | 0 | 0 |

*In determining the immortalizing efficiency the differing molar amounts of immortalizing DNA were not taken into account.

EXAMPLE 4

Immortalization of human lymphocytes by transfection with a DNA which was first incubated with a protein fraction from permanently culturable human or animal cells.

The immortalizing DNA sequences LC108 and EFC38 are amplified enzymatically as described in example 3. In addition the following protein fractions (N) and (C) are isolated:

Ehrlich ascites cells (10$^8$ cells) are resuspended in 50 mmol/l Tris, pH 7.4, 10 mmol/l EDTA, 3 mmol/l MgCl$_2$ and lysed by repeated freezing and thawing. The nuclei are separated from the cytoplasmic fraction (C) by centrifuging for 30 minutes at 6000×g. The nuclei are resuspended in 20 mmol/l Hepes, pH 7.9, 420 mmol/l NaCl, 1.5 mmol/l MgCl$_2$, 2 mmol/l EDTA, 10 mmol/l β-mercaptoethanol, 2 µg/ml aprotinin, 25% (v/v) glycerol in order to prepare the nuclear fraction (N). The nuclei are homogenized, sonified 2×1 min and centrifuged for 30 min at 25000×g, 4° C. The supernatant (nuclear fraction N) is dialysed against PBS. The cytoplasmic fraction (C) is centrifuged for 1 hour at 100000×g at 4° C. and the supernatant is dialysed against PBS. The RNA of the nuclear fraction (N) and of the cytoplasmic fraction (C) is degraded by incubation with RNase A (20 µg/ml) and RNase T1 (1000 U/ml) at 37° C. for 1 hour.

In order to produce EFC38 DNA/protein particles, 10 ng EFC38 DNA is incubated with 5 µl supernatant of the cytoplasmic fraction or of the nuclear fraction for 30 minutes at 4° C. in the presence of NaCl (80 mmol/l), Tris-HCl (10 mmol/l, pH 7.0, βmercaptoethanol (10 mmol/l), tRNA (600 ng/µl), herring sperm DNA (66 ng/µl), 1 mmol/l ATP, 1 mmol/l GTP. In order to produce the LC108 DNA/protein particles, 10 ng LC108 DNA is incubated with 5 µl cytoplasmic fraction or nuclear fraction in each case for 30 min at 4° C. in the presence of ZnCl$_2$ (8 mmol/1), Tris-HCl (10 mmol/l), pH 7.0, βmercaptoethanol (10 mmol/1), tRNA (600 µg/ml), herring sperm DNA (66 µg/ml), (1 mM ATP, 1 mM GTP). The proteins which have not bound to the respective DNA sequence are degraded by incubation with proteinase K (20 µg/ml) for 1 hour at 60° C.

The lymphocytes to be immortalized from peripheral blood were isolated as described in example 2.1. The lymphocytes are divided into 9 parallel cultures each of 10$^8$ cells. The cells are transfected as described in example 2.2: the cells of culture A with 10 ng LC108 DNA, each of the cultures B and C with 10 ng LC108 DNA which has been previously incubated with proteins of the cytoplasmic fraction (C) or nuclear fraction (N); culture D with 10 ng EFC38 DNA and each of the cultures E and F with 10 ng EFC38 DNA which has been previously incubated with proteins of the cytoplasmic fraction (C) or nuclear fraction (N). The cells of culture G are treated in the same way as the other cultures but without the presence of proteins or DNA. The cells of culture H are incubated with 5 μl cytoplasmic fraction (C), the cells of culture I with 5 μl nuclear fraction (N). The culture of the transfected and immortalized cells is carried out as described in example 2.2.

Continuously growing colonies of lymphoid cells are observed in cultures A to F which can be continuously passaged from the sixth week without observing any ageing of the cells. In the cultures which were transfected with DNA/protein particles, more immortalized colonies are obtained after transfection than with the respective DNA without protein incubation (Table 3). No cell proliferation is observed in cultures G, H and I. The cells die within the first week after transfection.

TABLE 3

Immortalization of human lymphocytes by transferring LC108 DNA/protein and EFC38 DNA/protein particles

| Cul-ture | Lympho-cytes used | Transfected DNA | (ng) | Protein fraction | Immortal. lymphoid colonies | Immort. efficiency* colonies/ng DNA |
|---|---|---|---|---|---|---|
| A | $10^8$ | LC108 | 10 ng | — | 35 | 3.5 |
| B | $10^8$ | LC108 | 10 ng | C | ca. 200 | 20 |
| C | $10^8$ | LC108 | 10 ng | N | ca. 170 | 17 |
| D | $10^8$ | EFC38 | 24 ng | — | 34 | 1.4 |
| E | $10^8$ | EFC38 | 24 ng | C | ca. 90 | 3.7 |
| F | $10^8$ | EFC38 | 24 ng | N | ca. 100 | 4.2 |
| G | $10^8$ | — | — | — | 0 | 0 |
| H | $10^8$ | — | — | C | 0 | 0 |
| I | $10^8$ | — | — | N | 0 | 0 |

*In determining the immortalizing efficiency the differing molar amounts of immortalizing DNA was not taken into account.

EXAMPLE 5

Use of immortalized human lymphocytes for testing the neoplastic transforming activity of alkylated nitroso carcinogens.

The immortalized human lymphocytes obtained according to example 2 do not express a neoplastically transformed phenotype. Thus these cells do not form colonies in semi-solid agar medium. In contrast tumour cells grow in such a medium.

Growth in semi-solid agar medium can be induced by incubation of the immortalized cells with carcinogenic substances in vitro. Colony formation of the immortalized cells in this medium is thus an indication of a possible transforming activity of the corresponding substance.

1. Incubation of the cells with the substance to be tested

Immortalized human lymphocytes are obtained as described in example 2 by transfection with LC108 DNA (SEQ ID NO:1) 1) or EFC38 DNA (SEQ ID NO:2). The immortalized lymphocytes are cultured at 37° C. and 5% $CO_2$ in Iscove's DMEM with 10% fetal calf serum, washed with PBS and resuspended in serum-free Iscove's DMEM, pH 6.0 at a cell density of $10^6$ cells/ml. Subsequently the cells are incubated for 30 minutes at 37° C. with 0.1–100 μg/ml 1-nitroso-1-urea (NMU) or 0.001–2 μg/ml N'-methyl-N- nitro-N-nitroso-guanidine (MNNG). Subsequently the cells are washed with PBS. 2. Determination of the colony formation in semi-solid agar medium In order to test colony formation in semi-solid agar medium, 3 ml of a 0.5% Seaplaque agar solution (FMC, Rockland, USA) in Iscove's DMEM with 10% fetal calf serum is placed in a 60 mm petri dish. When the agar has set, the cells obtained according to 1. are resuspended in 3 ml of a 0.35% agar solution in Iscove's DMEM (3 parallel preparations each with $5\times10^5$, $1\times10^6$ or $5\times10^6$ cells in 3 ml) and applied to the agar plates. The cells are incubated for 2 to 3 weeks at 37° C., 5% $CO_2$. The colonies which grow during this time are then counted under a stereoscopic microscope. The results are summarized in Table 4.

TABLE 4

Colony formation of immortalized lymphocytes in semi-solid agar medium after incubation with NMU or MNNG

| Carcinogen | Concentration (μg/ml) | Number of colonies in soft agar per cells used | Cloning efficiency |
|---|---|---|---|
| — | — | $0/10^7$ cells | $<10^{-7}$ |
| NMU | 0.1 | $15/10^6$ cells | $1.5 \times 10^{-5}$ |
|  | 1.0 | $82/10^6$ cells | $8.2 \times 10^{-5}$ |
|  | 10 | $250/10^6$ cells | $2.5 \times 10^{-4}$ |
|  | 20 | $300/10^6$ cells | $3.0 \times 10^{-4}$ |
| MNNG | 0.001 | $10/10^6$ cells | $1.0 \times 10^{-5}$ |
|  | 0.01 | $90/10^6$ cells | $9.0 \times 10^{-5}$ |
|  | 0.1 | $540/10^6$ cells | $5.4 \times 10^{-4}$ |
|  | 1.0 | $1800/10^6$ cells | $1.8 \times 10^{-3}$ |
|  | 5.0 | $4000/10^6$ cells | $4.0 \times 10^{-3}$ |

We claim:

1. An isolated nucleic acid molecule which consists of the nucleotide sequence set forth in SEQ ID NO:1 or SEQ ID NO:2.

2. An isolated nucleic acid molecule which hybridizes to the nucleic acid molecule of claim 1 under stringent conditions and which immortalizes a host human cell or animal cell when transfected therein.

3. A human cell line or an animal cell line transfected with the isolated nucleic acid molecule of claim 1.

4. A human cell line or an animal cell line transfected with the isolated nucleic acid molecule of claim 2.

5. The human cell line of claim 3, wherein said human cell line is a human lymphocyte cell line.

6. A process for isolating a nucleic acid molecule which immortalizes a human lymphoblast or lymphocyte or an animal lymphoblast or lymphocyte when transfected therein, comprising:

(i) separating nuclear and cytoplasmic fractions of permanently culturable human cells or animal cells, (ii) removing mitochondria from said cytoplasmic fractions to form mitochondria free cytoplasmic fractions, (iii) contacting said mitochondria free cytoplasmic fractions with Rnase and proteinase to digest RNA and protein in said mitochondria free cytoplasmic fractions, (iv) separating a DNA containing fraction from said mitochondria free cytoplasmic fractions resulting from step (iii), wherein said DNA containing fraction has a density of about 1.86 g/cm$^3$, (v) contacting said DNA containing fraction with at least one nucleic acid having the nucleotide sequence of SEQ ID NO:1 or the nucleotide sequence of SEQ ID NO:2 to hybridize the DNA in said DNA containing fraction to said nucleic acid, and (vi) isolating the hybridized DNA therefrom.

7. A process for isolating a nucleic acid molecule which immortalizes human lymphoblasts or lymphocytes or animal lymphoblasts or lymphocytes comprising:

(i) lysing a whole cell sample to produce a nuclear DNA free cell fraction, (ii) centrifuging said nuclear DNA free cell fraction to produce a cell fraction having a density of about 1.86 g/cm$^3$, which cell fraction contains said nucleic acid molecule, (iii) contacting said cell fraction containing said nucleic acid molecule with at least one nucleic acid having the nucleotide sequence of SEQ ID NO:1 or the nucleotide sequence of SEQ ID NO:2, to hybridize the DNA in said cell fraction containing said nucleic acid molecule to said nucleic acid, and (iv) isolating the hybridized DNA therefrom.

8. The process of claim 7, wherein step (i) comprises lysing said whole cell sample with sodium chloride and sodium dodecyl sulfate.

9. An expression vector comprising the isolated nucleic acid molecule of claim 1, operably linked to a promoter.

10. A method for producing an immortalized human cell or animal cell, comprising contacting a normal human cell or animal cell with the isolated nucleic acid molecule of claim 2 under conditions favoring transfection thereby, and culturing the resulting transfected cell in the absence of selection media.

11. A method for producing an immortalized human lymphoblast or lymphocyte, or an immortalized animal lymphoblast or lymphocyte, comprising transfecting a normal cell selected from the group consisting of a human lymphoblast, a human lymphocyte, an animal lymphoblast, and an animal lymphocyte with the isolated nucleic acid molecule of claim 1, and culturing said cell in the absence of selection media.

12. The method of claim 11, further comprising stimulating said normal human lymphoblast or lymphocyte, or said normal animal lymphoblast or lymphocyte to divide prior to said transfection with said isolated nucleic acid molecule.

13. A method for producing immortalized human lymphoblasts or immortalized animal lymphoblasts, comprising transfecting $10^8$ normal human lymphoblasts or $10^8$ normal animal lymphoblasts with about 10–30 ng of the isolated nucleic acid molecule of claim 1, and culturing said normal human lymphoblasts or normal animal lymphoblasts in the absence of selection media.

14. An oligonucleotide molecule which consists of a 20 to 30 nucleotide fragment of the nucleotide sequence set forth in SEQ ID NO:1 or a 20–30 nucleotide fragment of the nucleotide sequence set forth in SEQ ID NO:2.

15. A method for amplifying at least one of (i) the nucleic acid molecule of SEQ ID NO:1 or (ii) the nucleic acid molecule of SEQ ID NO:2, comprising:

contacting a sample containing at least one of the nucleotide sequences set forth as SEQ ID NO:1 or SEQ ID NO:2 with the oligonucleotide molecule of claim 14 and an amplifying enzyme to amplify at least one of the nucleotide sequences set forth as SEQ ID NO:1 or SEQ ID NO:2.

16. The oligonucleotide molecule of claim 14, selected from the group consisting of: SEQ ID NO:3, SEQ ID NO:4, SEQ ID NO:5, and SEQ ID NO:6.

17. The method of claim 15 wherein said oligonucleotide molecule is selected from the group consisting of: SEQ ID NO:3, SEQ ID NO:4, SEQ ID NO:5, and SEQ ID NO:6.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 203 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

| | | | | | |
|---|---|---|---|---|---|
| GATCTTGAGT | TTCCTCGTTG | TAGGTCTTCC | CTGGCTCTGC | TCACGCTCTC | ACTGACTTCT | 60
| CTCAGCTCAG | TCACAGTGTC | TATTTCTTTC | CACTTAAAGA | TGTGCATTTT | TATTTGATGC | 120
| GTGCAGGTGT | TTTGCCTGCA | TGGATGGCTG | TGCACCATGT | ATGGACCTG | GTGCTCTTGG | 180
| AGGCCAGCAG | AGGGCTTTGG | ATC | | | | 203

( 2 ) INFORMATION FOR SEQ ID NO: 2:

( i ) SEQUENCE CHARACTERISTICS:
        ( A ) LENGTH: 376 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 2:

| | | | | | |
|---|---|---|---|---|---|
| GATCCAATCA | GCTCAGCCAC | CCCCAGCTCT | CCTGTATGTA | TGGCTCCAAT | GCTGTTCATC | 60
| CCTCAGCATA | AATCAATCAT | TTGGTTTAGA | TTCCTCCCTT | TGACTTATTG | CTACTATTAG | 120
| TATCAGTGAC | TCTTCAGCCG | ATTCTTTTCA | GACATTGGAA | CCCCAGCCTC | AGATCACAGT | 180
| TGTAGAACAA | ATATTAAAAG | AGTAAATTAT | TATATCATTG | AACATTCAAA | AGTGCTTTGC | 240
| AGTCATTGAC | ACATAATAAT | AATGAAGCCT | AAACAGTAAC | ATGAAAATGT | GGAATTGTAT | 300
| TAATGTAAAA | TCAAGGCCTG | GGGCATAGCT | CATTGGTGGA | TGTTTGCCTA | TCATGTGGGA | 360
| GGCCCTGGTT | TTGATC | | | | | 376

( 2 ) INFORMATION FOR SEQ ID NO: 3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

| | | |
|---|---|---|
| GATCTTGAGT | TTCCTCGTTG | TAGGT | 25

( 2 ) INFORMATION FOR SEQ ID NO: 4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

| | | |
|---|---|---|
| GATCCAAAGC | CCTCTGCTGG | CCTCC | 25

( 2 ) INFORMATION FOR SEQ ID NO: 5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

| | | |
|---|---|---|
| GATCCAATCA | GCTCAGCCAC | CCCCA | 25

( 2 ) INFORMATION FOR SEQ ID NO: 6:

( i ) SEQUENCE CHARACTERISTICS:
        ( A ) LENGTH: 25 base pairs
        ( B ) TYPE: nucleic acid (C) STRANDEDNESS: single
(D) TOPOLOGY: linear (xi) SEQUENCE DESCRIPTION: SEQ ID NO: 6:

GATCAAAACC AGGGCCTCCC ACATG    25